United States Patent [19]

Nunes et al.

[11] Patent Number: 5,073,630
[45] Date of Patent: Dec. 17, 1991

[54] POLYMERIC ANHYDRIDE OF MAGNESIUM AND PROTEIC AMMONIUM PHOSPHOLINOLEATE WITH ANTIVIRAL, ANTINEOPLASTIC AND IMMUNOSTIMULANT PROPERTIES

[75] Inventors: Odilon D. Nunes, Birigui; Nelson E. C. Durán, Campinas, both of Brazil

[73] Assignee: Nunes & Duran Pesquisa Comercio e Desenvolvimento Ltda., Sao Paulo, Brazil

[21] Appl. No.: 527,581

[22] Filed: May 23, 1990

[30] Foreign Application Priority Data

May 30, 1989 [BR] Brazil ............................... PI8902936

[51] Int. Cl.$^5$ ............................................. C07K 15/22
[52] U.S. Cl. .................................. 530/400; 435/68.1; 530/352
[58] Field of Search ................ 405/68.1; 530/352, 400

[56] References Cited

U.S. PATENT DOCUMENTS 4,855,284  8/1989  Emoedi ............................... 530/395

Primary Examiner—Howard E. Schain

[57] ABSTRACT

The invention relates to a polymeric anhydride of magnesium and proteic ammonium phospholinoleate having the following distribution of components expressed in percentage of magnesium (20.1±0.9%), Ammonium (10.0±3.3%), Phosphate (45.2±2.7%), linoleic acid (11.6±4.3%), total protein (0.49±0.07%) with the presence in percentage of the following aminoacids: Aspartic Acid (7.19%), Threonine (3.56%), Serine (7.56%), Glutamic Acid (8.53%), Proline (0.5%), Glycine (9.69%), Alanine (7.46%), Valine (1.0%), Methionine (4.38%), Isoleucine (2.54%), Leucine (3.03%), Thyrosine (0.5%), Phenylanine (1.0%), Histidine (2.83%), Lysine (3.56%), Tryptofan (1.3%) and Arginine (35.2%).

This compound is produced from a selected line of Aspergillus sp in culture of oat schaff and bouillon at the temperature of 30°/35° C., pH 3-4 with low aeration (10 l/m) and agitation (40 rph) restricted to the first 48 hours of the producing process. After 120 hours of fermentation, the fermented mass is filtrated, washed with water and acetone and the solution precipitated at pH 11, and the precipitated crystals being finally washed with sulphuric ether and then dried.

2 Claims, 11 Drawing Sheets

LEGEND (A) POLYMERIC ANHYDRIDE + EDTA (—) ALBUMIN

POLYMERIC ANHYDRIDE OF MAGNESIUM AND PROTEIC AMMONIUM PHOSPHOLINOLEATE WITH ANTIVIRAL, ANTINEOPLASTIC AND IMMUNOSTIMULANT PROPERTIES

The present invention relates to a new polymeric anhydride of magnesium and proteic ammonium phospholinoleate as well as to the process for its production.

Until now the treatment of viral pathologies was limited to prophylaxis via systematic vaccination.

Partially because of the efficiency of such vaccines small efforts have been made to reach the development of specific agents for attacking such infections.

Nevertheless the lack of an efficient vaccine to attack several types of viruses calls for the existence of a therapeutically trustable drug for these affections.

Within this field and during the last years some drugs have proved to be efficient in "in vitro" and "in vivo" experiments even if for a clinical use but subject to several restrictions due to toxicity problems.

Acyclovir constitutes an exception and proved to be successful in connection with infections caused by Herpes Virus. Similar considerations are applicable in connection with anticancer drugs.

Notwithstanding all advances obtained with respect to antineoplastic chemotherapy, all drugs which have been developed till now show a great level of cytotoxicity "in vitro" and "in vivo" thereby causing serious obstacles to the clinical use.

It is of general acceptance that immunostimulation constitutes an alternative to the conventional chemotherapy, specially when the host's defense mechanism has to be activated under conditions of decrease of the immunological responsiveness. For instance, it is of prime importance in case of treatment of chronic and/or antibiotic therapy persistant infections.

Another field of application is the prophylaxis of infections in patients at risk, where the utility of an immunostimulant drug is evident.

The object of the present invention is situated inside the above parameters and such object may be defined as follows: a polymeric anhydride of magnesium and proteic ammonium phospholinoleate having antiviral, antineoplastic and immunostimulant properties.

In order to develop the compound of the present invention having the mentioned characteristics the following biological properties of isolated components have been used as starting points:

A) MAGNESIUM

Biological Properties

Magnesium has not shown any toxicity in Ames Test. $MgSO_4$ has not shown embriotoxic effects and $MgCl_2$ has shown low toxicity. Patients treated with magnesium lactate (oral) three times a day have shown a meaningful improvement in 70% of the cases of Tetanus.

Experiments involving human foreskin fibroblast in the presence of the vesicular stomatitis virus have shown that $Mg^{+2}$ ion increases the production of Interferon and the antiviral activity of poly (A-U) and poly (G-C). The number of esophagus tumor in BD IX mice treated with N-nitromethylbenzylamine has been substantially reduced when the mice were treated with $Mg^{+2}$. "In vitro" magnesium stimulates the production of lymphocytes-T. $Mg^{+2}$ defficiency causes a dramatical fall in the primary and secondary immune response when measured by the number of hypophysis AFC of C57 B1/6 mice.

Magnesium defficient diets in mice induce disturbances in the immunological mechanism thereby causing decrease of the survival expectation as a result of the exposure to radiation. When the ion is replaced to the diet such effects disappear.

Magnesium supports the linkage of IgM complex with mice lymphocytes, but not with macrofages. Linkage with IgG complex does not depend on the cation.

B) LINOLEIC ACID

Linoleic acid has shown low leucocite toxicity. It has been observed a decrease of 10% in RNA synthesis in concentrations of 10 ug/ml. This acid is highly active against the enveloped viruses (vesicular-stomatitis virus, herpes simplex and visna virus) and does not show interaction with polio virus. This acid causes a great occurrence of cell death in cases of esophagus and breast carcinoma cell lineages. Fluidity of the tumoral cell membranes has been observed when sarcoma cells have been incubated with esters of linoleic acid.

Infection of cells treated with this acid has resulted in few mestastasis in lungs when compared to non-treated cells. Feeding of mice with cereal and ration and with the addition of 10% of linoleic acid has caused acceleration of the mobilization of the defense mechanisms of the mice against inoculation of microbial vaccine. Enveloped viruses are turned inactive in few minutes of contact with 5-25 ug concentrations of linoleic acid. In said concentrations linoleic acid has proved to be inocuous "in vitro" to the cells of the host animal. Non-enveloped viruses have not been affected by this acid (polio, SV-40 or EMC).

C) ARGININE AND POLYARGININE

Biological Properties

Polyarginine has proved to have no effect over the proliferation of fibroblasts in culture of human embryo and has also proved to be atoxic in AMES test. Arginine is required to express the activation mechanism of the macrofages thereby causing selectivity during metabolic inhibition in cellular targets. Polyarginine is a powerful inhibitor of the growth of VXZ tumor lineages in hamsters.

Polyarginine inhibits 50% of the growth of the mosaic viruses (TMV). Arginine inhibits carcinogenesis induced by polyaromatics. Polyarginine has shown activity against toxoids of diphtheria and tetanus. Mice have been inoculated with BP 8 cells in their backs and after 30 minutes they have received polyarginine and it has been observed an increase of the tumoral adherence. It has also been noted the inhibiting effect of the arginine in breast carcinogenesis induced by polyaromatics. Experimental results suggest that arginine may be a nutritional support to correct immune depression in patients with stress.

D) POLYPHOSPHATES

Biological Activities

The U.S. Food Drug Administration has not found any evidences proving harmful effects caused by polyphosphates to the public when used in current values in food. "In vitro" AMES and cromossomial anomalies tests have been carried out by using fibroblast of Chinese hamster and have demonstrated that polyphosphates have not caused harmful effects during these tests.

Polysaccharides have been phosphorated with polyphosphate at the presence of terciary amines. All phosphates thus formed have proved to be active as Interferon inducers. Since none of the used polysaccharides has shown such an activity it is reasonable to assume that the active centers of such inducers reside in the phosphate groups.

According to the present invention the isolated compound has been integrated in a new polymeric structure by means of a biological via thereby resulting in a new compound with synergistic action from the biological point of view and having the aforesaid properties.

The figures which accompany the present application illustrate as follows:

FIGS. 5 and 5a show the fluorescence spectra of polymeric anhydride (4 mg/ml in 0.1N HCl) ($\lambda$ exc 287 nm). (--------) and of bovine albumine (4 mg/ml in 0.1N HCl) (———); FIGS. 5 and 5a correspond to the polymeric anhydride in the absence and in the presence of magnesium ions respectively.

GENERAL CHARACTERISTICS

The compound of the present invention is presented in the form of a crystalline white powder which is insoluble in $H_2O$ and in the major part of organic stable solvents and which has a high melting point (over 300° C.).

Figure 1:
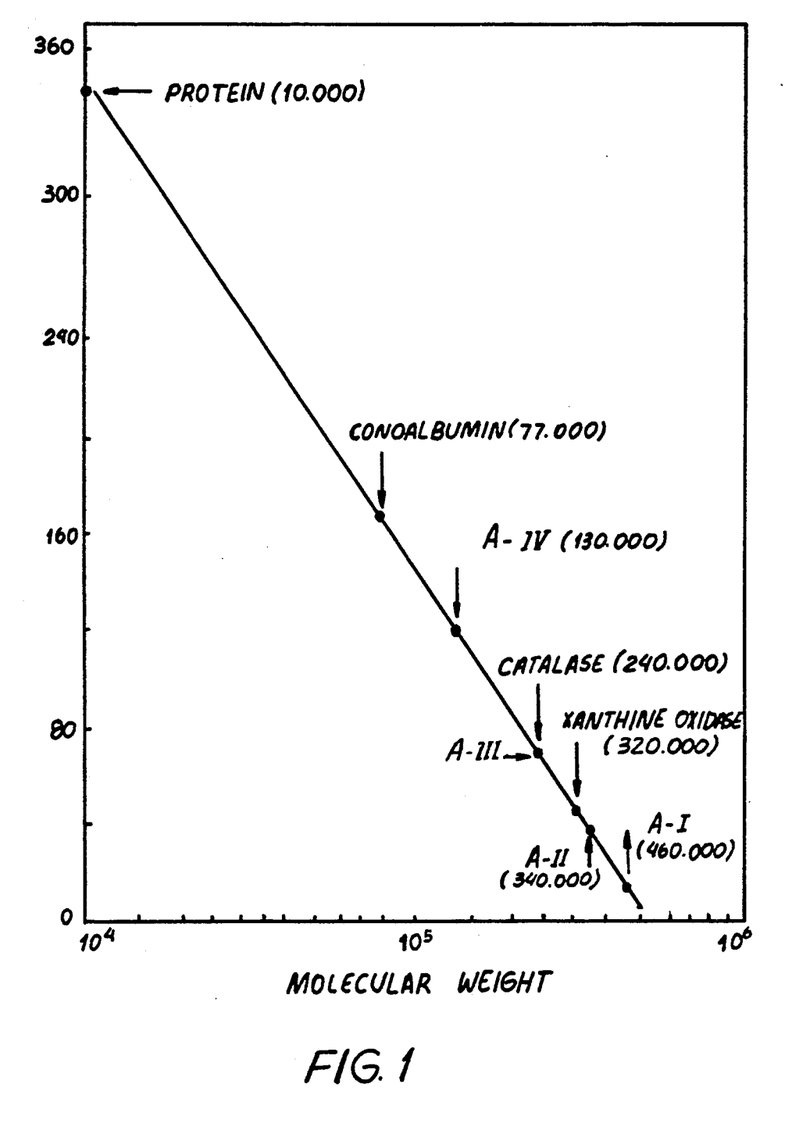
FIG. 1 shows the molecular weight determination of purified polymeric anhydride gel filtration chromatography with SEPHACRYL S-300 colum.

The average numerical molecular weight determined by filtration in SEPHACRYL S-300 in TRIS 0.02 m pH 8.0 was of 316.000 Daltons being represented by four fractions (AI, AII, AIII, AIV) (FIG. 1) and the following comparative protein markers have been used: conoalbumin (77.000 Daltons), catalase (240.000 Daltons) and xanthine-oxidase (320.000 Daltons).

The elementar analysis has enabled to set the following formula of the compound: $(C_{326}H_{614}O_{163}N_{204}S_2)y$ $x(C_{18}H_{35}Mg_2NO_{21}P_5)x$.

Electrophoretic characteristics are shown in Tables I and II, and chromatographic properties appear on Table III. Spectral properties are shown in Table IV.

Figure 2:
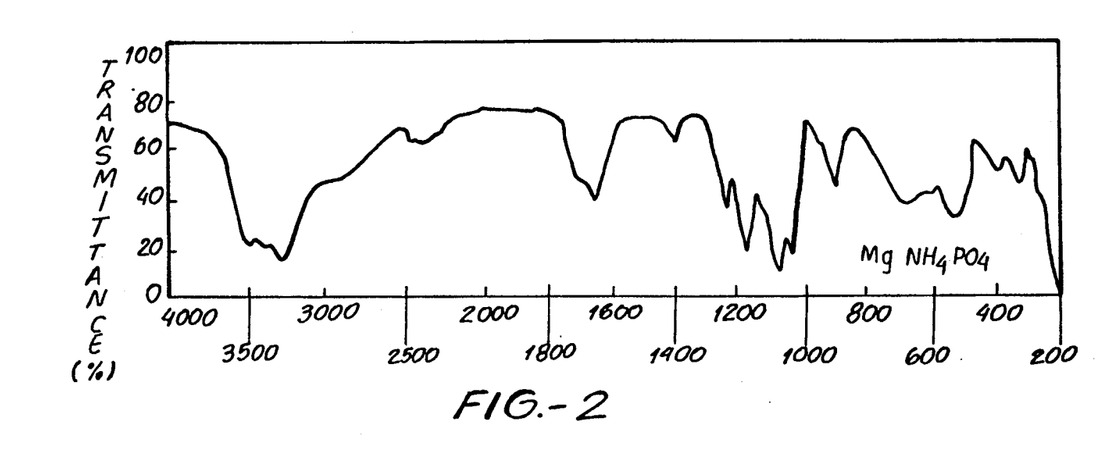
FIG. 2 shows the infra-red spectra in 0.5% KBr of $MgNH_4PO_4$.
Figure 2A:
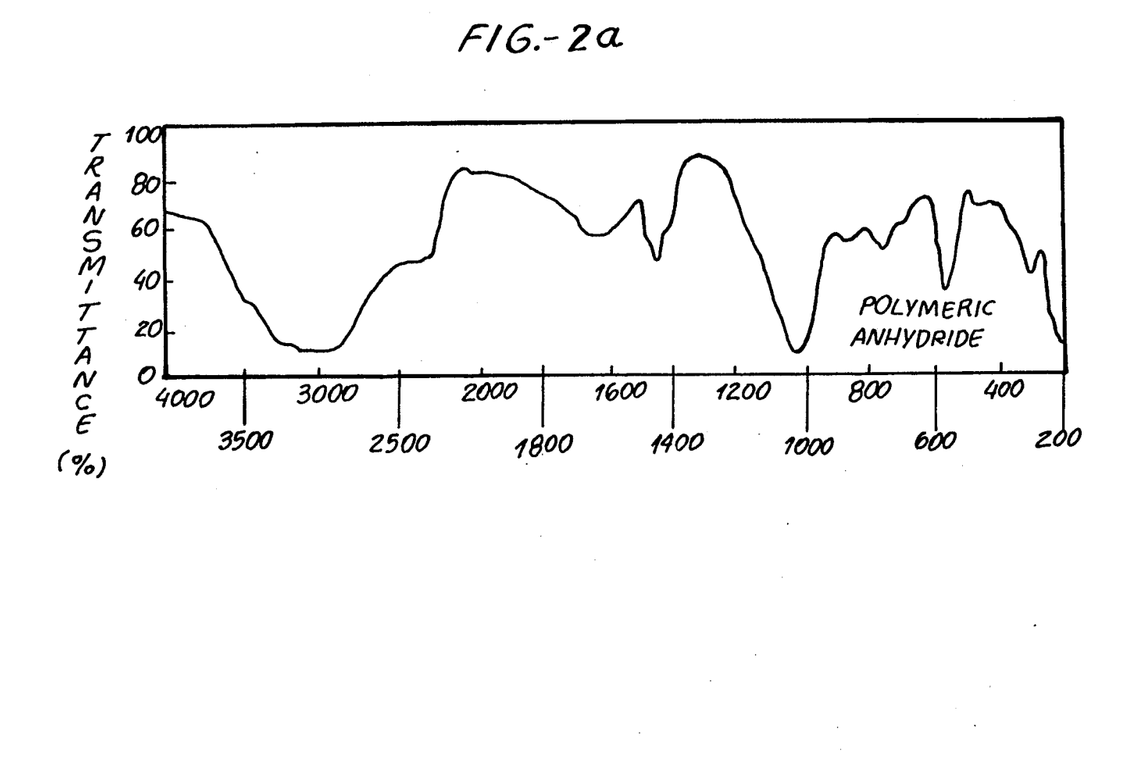
FIG. 2a shows the infra-red spectra 0.5% KBr of polymeric anhydride.
Figure 3:
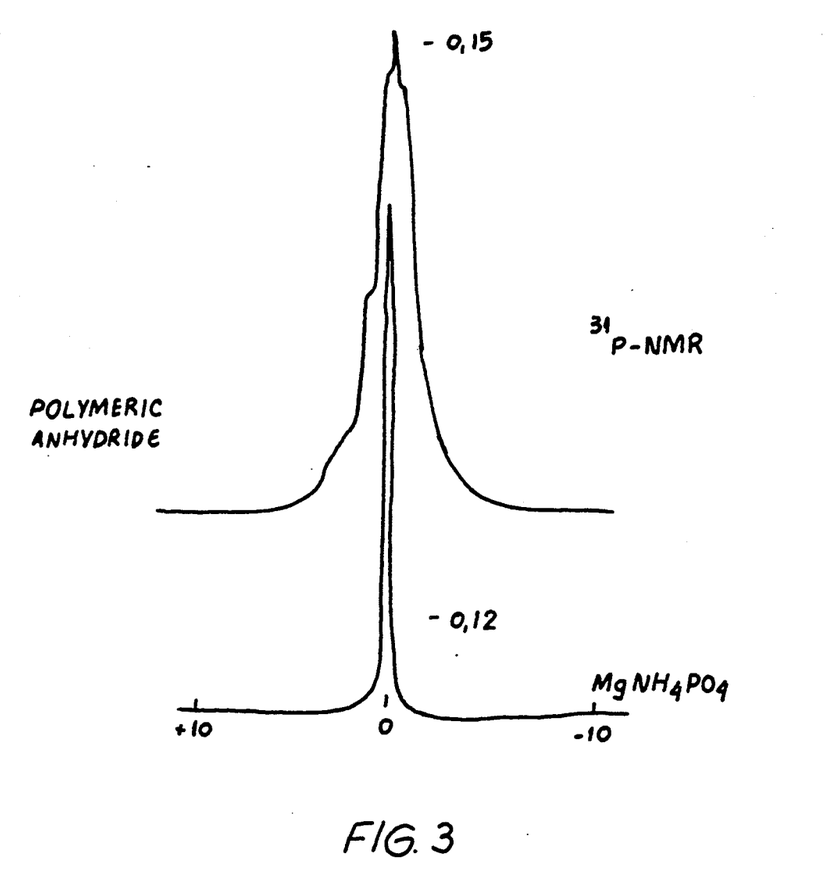
FIG. 3 shows the $^{31}P$-NMR spectra of polymeric anhydride and $MgNH_4PO_4$ (in 0.1M HCl solution).

It is important to point out the comparison between the new structure and a known compound such as salt $MgNH_4PO_4$ in infra-red (FIG. 2) as in $^{31}P$-NMR (FIG. 3). The mentioned methods clearly indicate the symmetry of the phosphate groups in $MgNH_4PO_4$ while the new structure shows asymmetrical phosphate groups. This shows the presence of an aggregate polymer and not of a linear phosphate polymer.

Figure 4:
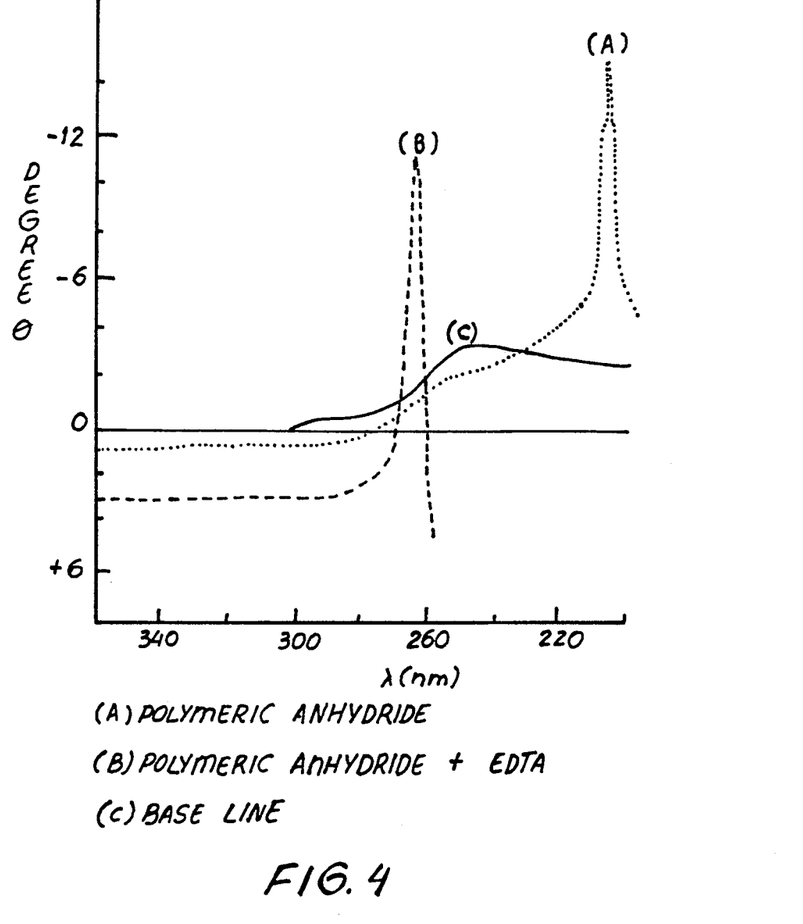
FIG. 4 shows the circular dichroism spectra of polymeric anhydride (4 mg/ml, 0.1 NHCl)(. . . ) and after 0.3M EDTA, pH 7.7 (------), base line (———).
Figure 5:
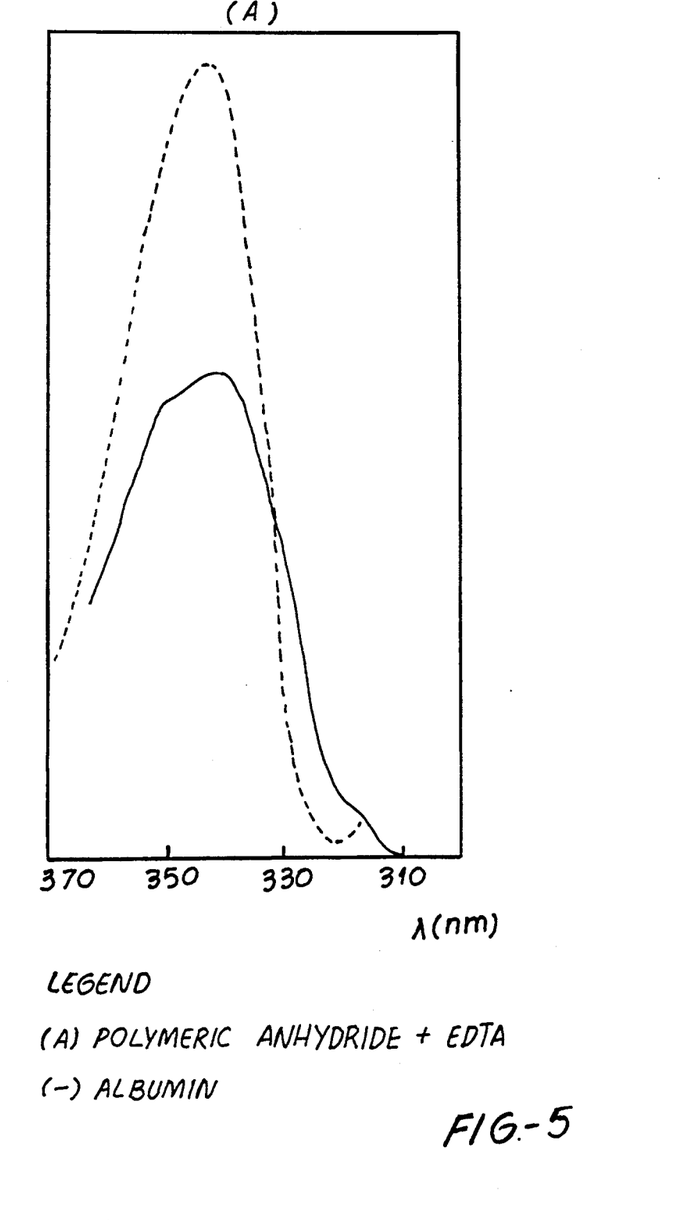
Figure 5A:
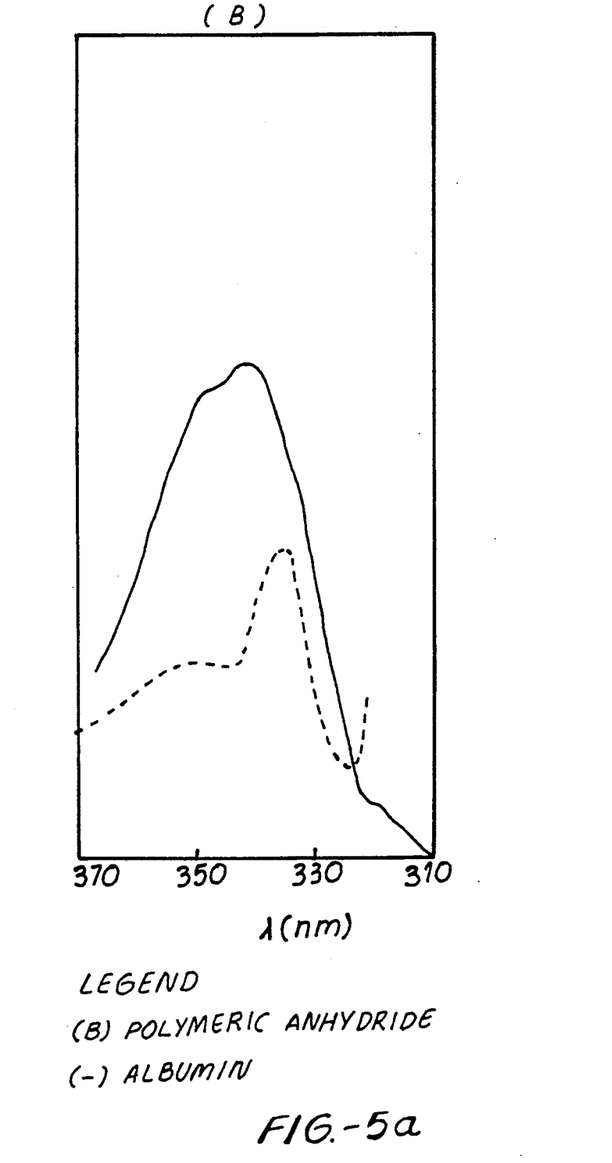

The importance of magnesium in the structure is observed in the circular dichroism (FIG. 4) and fluorescence (FIG. 5) wherein the presence of EDTA in solution with polymeric anhydride shows the same effect on the spectre lines of the graphic thereby indicating that magnesium performs a fundamental role in the stability of the compound.

Table II shows the electrophoretic behavior of the polymeric anhydride in aquous solutions thereby indicating that the compound suffers drastic changes in the structure after seven days in solution.

Polymeric anhydride shows a high sensibility to EDTA and DOWEX-50($Na^+$) because upon treating with such substances the solution becomes fully transparent with gradual disappearance of the opalescence. Dense crystals of the polymeric orthophosphate are precipitated when the solution is cool extracted with urea-ammonium and remains resting overnight. Such a precipitate does not dialyze at pH 9.0 to 11.0.

These properties permit the confirmation that magnesium and ammonium in addition to the organic part of the aggregate polymer are the determining factors which are able to determine the integrity of the molecule.

Figure 6:
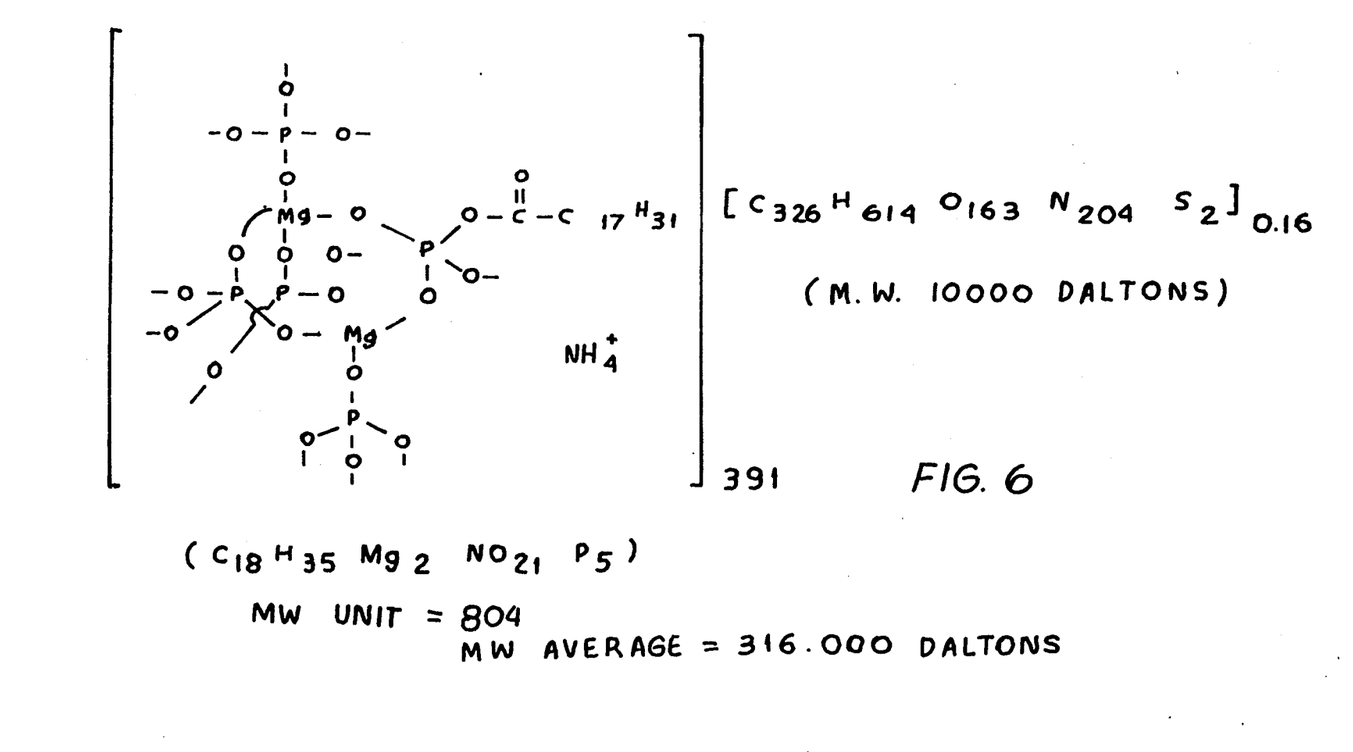
FIG. 6 shows the proposed polymeric anhydride structure.

The suggested structure of the polymeric anhydride (FIG. 6) has the following empirical formula: $MgO + 2.25\ P_2O_5$ with the presence of ammonium ion, protein and linoleic acid.

Figure 7A:
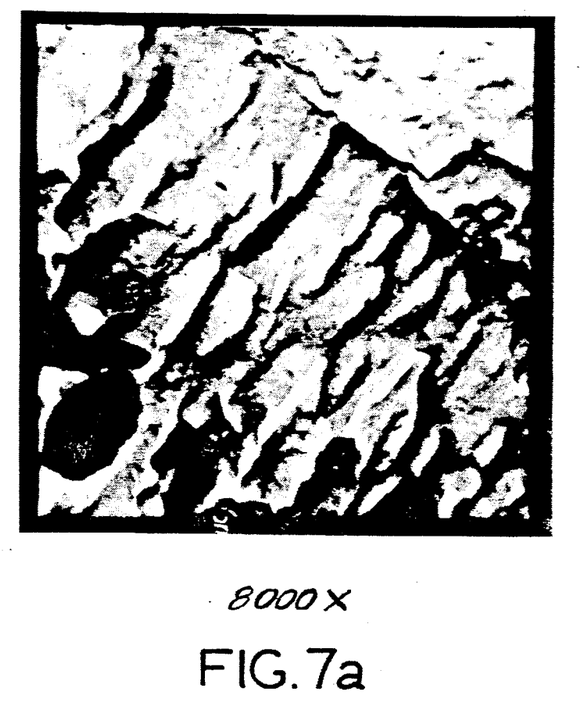
FIG. 7a shows the electron micrograph (8000× amplification) of the polymeric anhydride.
Figure 7B:
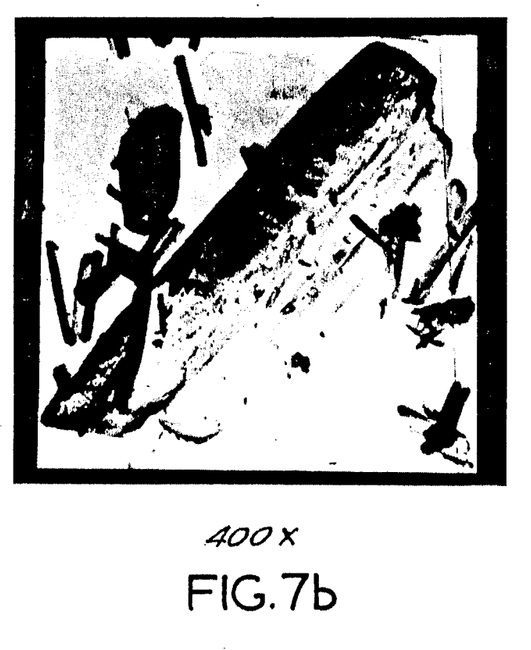
FIG. 7b shows the electron micrograph (400× amplifications) of the polymeric anhydride.
Figure 7C:
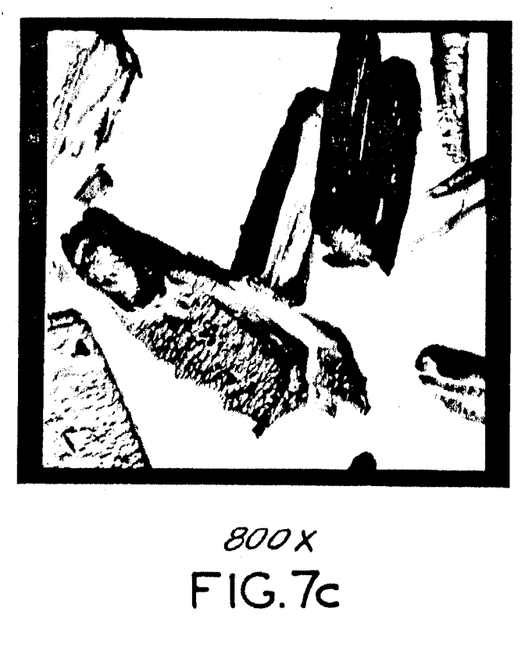
FIG. 7c shows the electron micrograph (800× amplifications) of the polymeric anhydride.

The characteristics of the aggregate may be observed from FIG. 7 which shows micrographies obtained by electronic scanning microscope at different increases showing crystal nettings.

Figure 8:
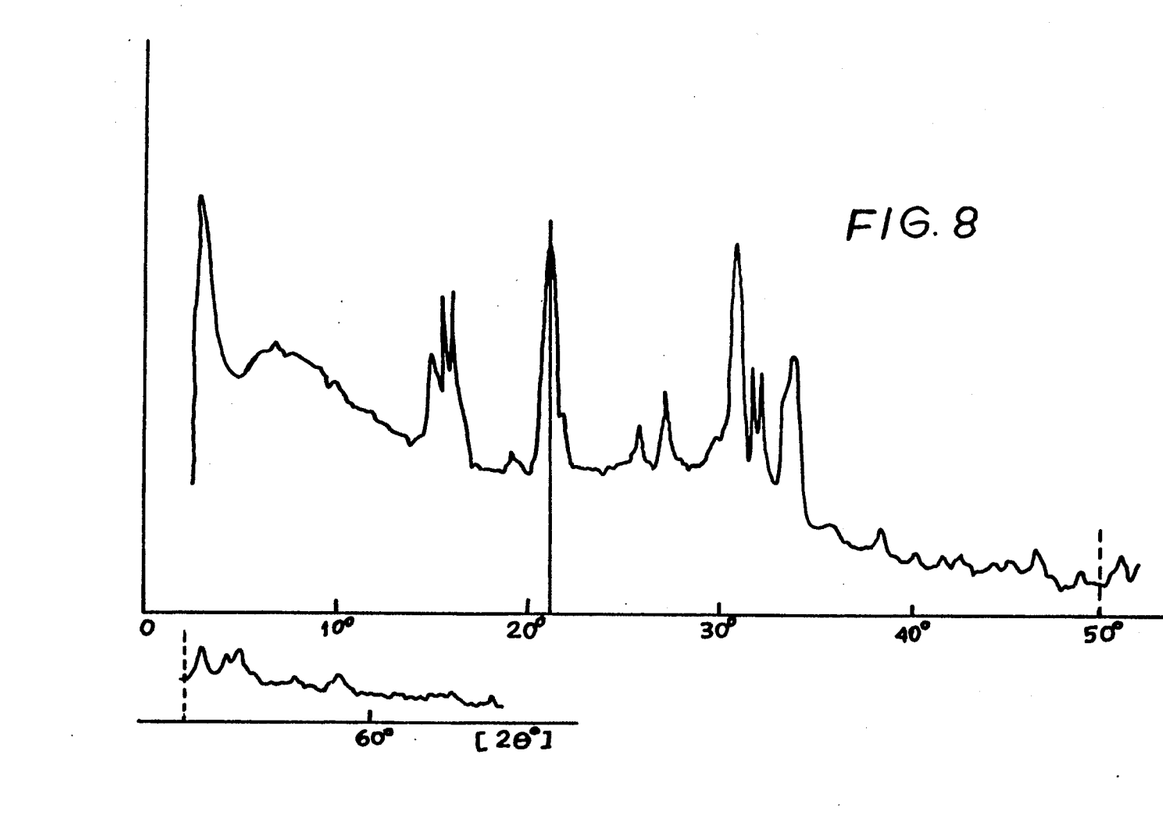
FIG. 8 shows the Debye-Scherrer diagram of polymeric anhydride.

Although the polymeric aggregate shows a fibrous aspect the diagram Debye-Scherrer in X-ray proves a certain grade of crystallinity (FIG. 8).

Upon considering all the information such as molecular weight, spectral characteristics, electronic microscopy, X-rays etc., we can affirm that the compound is a polymeric anhydride of magnesium and proteic ammonium.

BIOLOGICAL PROPERTIES

In order to show the potential of the present invention some characteristics are now shown as some examples, and no way limiting or causing restriction to the escope of the invention and to its field of practical application.

a) Antiviral Properties

With reference to the antiviral properties of the substances we have studied the "in vitro" action of the new molecule in Herpes Simplex 1 (HSV-I) and Adenovirus 5 by using methods current in the scientific literature (B. Rado, B. Blascovi, F. Storm, Skoda, Experimentia 16.487 (1960)).

HSV-1 has been completely inhibited with 0.13 uM (50 ug/ml) of the product.

With respect to the effect over Adenovirus 5, minimum values of inhibition of 0.25 uM (100 ug/ml) for our product have been found.

"In vivo" tests in animal virosis using the product of the present invention have shown 90% of recuperation in parvovirus Canine while the mortality in control groups was of about 100%.

These tests in a veterinary clinic have extended for over 5 years involving a lot of animals. During said experimental period no physiological or teratogenic alterations have been detected in animals treated with a therapeutic dosage which was standardized in 1 mg/kg by weight.

No embriotoxic alteration has been found in the descent of the animals treated with the new product.

b) Antineoplastic Properties

Experiments with Spl tumors in mice (spontaneous mammary carcinoma) and myeloma in balb/c mice have proved the potential of the new product as antineoplastic drug.

During these experiments tumors have been transplanted and upon reaching 0.5 cm the application of the product has been started (0.5 mg/animal, twice a week) by intraperitoneal via.

The tumoral growth has been checked twice a week and the results have shown that the animals treated with the substance of the present invention proved a significant inhibition of the tumoral growth, and therefore the survival of the animals inoculated with the product of the present invention has been extended in 30% in respect of the controls.

c) Immunological Capacity

Studies have been carried out in order to determine the effect of the substance of the present invention in cultures of spleen lymphocytes in Balb/c mice in the presence and in the absence of a blastogenesis inducer (Concanavalin A).

In low concentrations and in the absence of the inducer (1 ug/ml) the product of the present invention has shown a significant effect in mitogenesis of spleen lymphocytes. The efficiency of the product shown by the experiments is comparable to Concanavalin A which is a known blastogenesis mitogenic inducer in the same concentrations.

"In vivo" experiments using Swiss albine mice inoculated with 2 mg/animal have shown a positive production of IgG with respect to the controls after 72 hours of inoculation.

CYTOTOXICITY OF THE NEW COMPOUND

"In vitro" cytotoxicity of the compound has been determined in V-79 cell line (Chinese hamster fibroblast). The compound has not shown any cytotoxic effect of 100 ug/ml.

The compound of the present invention has proved to be atoxic in concentrations for mytochondrial rat liver in respiration as well as in oxidative phosphorylation and calcium transportation.

Studies of the proliferous response of the present compound over splenic lymphocytes of Balb/c mice in culture and at the presence of an inducer have also been carried out. In concentrations of 100 ug/ml the substance of the present invention inhibits 74% of proliferative response.

COMPARED CYTOTOXICITY

In order to establish the parameters of use of the new compound we have compared it with antiviral substances of current use in therapeutics. Two substances have been chosen: Idoxuridine and Acyclovir.

The scientific literature (C. S. Crumpacker, L. E. Sclinipper, I. A. Zala e M. I. Levin, Antimicrob. Agents Chemother, 15.642 (1979)) shows a value of $LD_{50}$ in mice by oral via of 10 g/Kg and 1 g/Kg by intraperitoneal via for Acyclovir.

Idoxuridine however shows severe toxic effects in animals and cellular cultures (I. C. Kelley and L. Beauchamp, Ann. Repart. Med. Chem. 18, 139 (1983)).

The lethal dose (LD 50) for the product of the present invention was of approximately 2.71/day 1.55 g/kg in mice intraperitoneally inoculated. Oral injection up to 30 g/Kg did not exert any lethality during 14 days of observation.

In studies with mice fibroblast cells, LM and RK-13 lineages, Acyclovir has shown cytotoxicity in concentrations of 17 uM (4 g/ml) as per R. L. Davidson, E. R. Kauffan, C. S. Crumpacker and L. E. Sclinipper Virology, 113 (1981). Idoxuridine has proved to be toxic in dosage of 1.4 uM (0.5 ug/ml) (N. K. Aysi, V. S. Gupta, J. B. Meldrun, A. K. Taneja and L. Babiouk and Agents Chemother, 17.558 (1980)).

Experiments involving survival curves of the Chinese hamster fibroblasts have shown that the product of the present invention is atoxic up to concentrations of 0.3 uM (120 ug/ml).

Experiments of cellular proliferation using V-79 lineage have been carried out in concentrations of 500 ug/ml and the results were the following:

74% for the product of the present invention
4.1% for Idoxuridine
80% for Acyclovir Therefore Idoxuridine has proved to be highly toxic and immunosuppressive while Acyclovir and the product of the present invention have not shown any relevant immunotoxicity.

However the product of the present invention has proved to be an IgG inducer in mice and with mytogenic capacity in cultures of lymphocytes. The same does not occur with Acyclovir and with Idoxuridine.

In summary, characteristic biological activities have been found when the compound was inoculated in cells or in animals.

No "in vitro" nor "in vivo" significant toxic effects have been observed able to interfere with the therapeutic activity. Therefore, the product of invention may be considered as a drug of low toxicity with antiviral, antineoplastic and immunostimulant properties.

OBJECTIVES

Taking into consideration all the above facts, the present invention provides for a compound defined with multiple biological activities covering the cited aspects.

It is an object of the present invention to offer a simple and economic bioprocess to produce a polymeric anhydride of magnesium and proteic ammonium phospholinoleate.

It is another object of the present invention to provide for a defined compound with antiviral, antineoplastic and immunostimulant properties.

According to the present invention, the polymeric anhydride of magnesium and proteic ammonium phospholinoleate is produced from a selected line of Aspergillus sp obtained by means of a paramorphic selection of a wild Aspergillus sp.

Fungal mycelium produces the compound when developed in a complex medium containing oat schaff and beef bouillon at a rate of 100/1 (schaff/bouillon) as nutrients.

After 120 hours of cultivation and the fermenter temperature being stabilized in the range of 30°/35° C., pH of the culture medium being kept in the range of 3/4; with low aeration (10 l/m) and agitation 40 (RpH) restricted to the initial 48 hours of the fermenting process. The fermented bouillon remains resting, the compound is precipitated at basic pH (11) after mechanical separation of mycelium and washing of the fermented mass with water and acetone at the rate of 40:1 (water:acetone).

The precipitated crystals are subject to washing with sulphuric ether for removal of impurities and then dried.

The resulting compound has the following distribution of components in percentage: Mg (20.1±0.9%), $NH_4$ (10±3.3%), Phosphate (45.2±2.7%), protein (0.49±0.07%) and linoleic acid (11.6±4.3%).

The rate phosphate/magnesium is of 2.25, phosphate/nitrogen is of 3.2, phosphate/protein is of 92.2 and phosphate/linoleic acid is of 3.9.

The average molecular weight determined by filtration in SEPHACRYL S-300 was of 316.000 Daltons.

The chromatographic analysis of lipide shows that this is the linoleic acid.

The content of aminoacid is distributed (9/100 g protein) as follows: Asp (7.19%), THR (3.56%), SER (7.56%), GLU (8.53%), PRO (0.5%), GLY (9.69%), ALA (7.46%), VAL (1.0%), MET (4.38%), ISOLEU (2.54%), LEU (3.03%), TYR (0.5%), PHE (1.0%), HIS (2.83%), LYS (3.56%), TRP (1.3%) and ARG (35.2%).

The inorganic part of the compound is constituted by Mg cations measured by atomic absorption.

The presence of phosphate ions has been determined by the Molybdate/Zinc acetate method. Ammonium ions have been quantitatively determined by electrochemical methods.

TABLE I

ELECTROPHORESIS IN WHATMAN PAPER No. 1 (12 V/cm) (a)

| BUFFER (ph) | MOBILITY |
|---|---|
| Acetate 0.05M (2.1) | — |
| Carbonate 0.05M (9.7) | — |
| Carbonate 0.05M (11.0) | 0.0 |
| Carbonate 0.05M (12.5) | + | a) The compound has been dissolved in dimethylsulphoxide.

TABLE II

ELECTROPHORESIS IN GEL

| | MOBILITY ($cm^2 volt^{-1} m^{-1}$) |
|---|---|
| Aggregated Orthophosphate (b) | (two bands) 1.1 and 1.3 |
| Hydrolyzed Aggregated Orthophosphate (a) | (one band in the origin) |
| Bovine Albumine | (three bands) 1.1:0.92 and 0.8 | a) Original samples which have been kept in PBS buffer for a week in the refrigerator.
b) The samples which have been analysed in solutions of 20 mg (100 ul) HCl 0.1N completed at 200 ul with TRIS-Glycine buffer (0.01M pH 8 3). It has been added 1 ul of bromophenol at 30 ul of the solution and 5 ul of the glycerol. This solution has been applied to the gel. The applied voltage was of 50 mV for 10 minutes and then 30 mV during 6 hours. Gel has been stained with silver nitrate. Gel has been prepared with 7.5% of acrylamine in the lower part and 3.5% of acrylamine and 0.3% of agarose in the upper part.

TABLE III

| | CHROMATOGRAPHIC PROPERTIES (a) | |
|---|---|---|
| | Rf | |
| PHASE (solvent) | Polymeric Aggregate | Linoleic |
| (b) | | |
| Silicium Gerl Merck (n-butyl alcohol/acetone (4:1)) | 0.50 | 0.86 |
| (Benzene/Acetone (2:1)) | 0.51 | 0.44 |
| Whatman No. 1 | | |
| (Benzene/Acetone (2:1)) | 0.02 | 0.85 |
| (Methanol/Acetone/$H_2O$ (60:20:2)) | — | 0.80(c) | a) Compound dissolved in dimethylsulphoxide
b) Compound dissolved in 0.5M EDTA and extracted with ether.
c) Rf of pure linoleic acid is 0.80.

TABLE IV

SPECTRAL PROPERTIES

UV (0.1N (HCl) λ max 205 nm, λ max 265 nm
UV (0.3 EDTA, pH 7.7) λ max 275 nm
IR (Kbr) 3400–2900 $cm^{-1}$, 1650–1600 $cm^{-1}$, 1450 $cm^{-1}$, 1000 $cm^{-1}$, 870 $cm^{-1}$, 750 $cm^{-1}$, 570 $cm^{-1}$
Fluorescence (0.1N HCl) λ exc. 295 nm, λ em. 340 nm
$^{31}$P-NMR (40.5 MHz) (0.1N HCl) δ = −0.15 (using $H_3PO_4$ as δ = 0)
CD (4 mg/ml) HCl 0.1N ⊖ 200 nm
(3 mg/ml) EDTA 0.3M pH 7.7, ⊖ 260 nm

We claim:

1. A polymeric anhydride of magnesium and proteic ammonium phospholinoleate with antiviral, antineoplastic and immunostimulant properties comprising: a content of Mg of 20.1±0.9%, $NH_4$ of 10.0±3.3%, phosphate of 45.2±2.7%, protein of 0.49%, linoleic acid of 11.6±2.83% and the following amino acids: ASP of 7.19%, THR of 3.56%, SER of 7.56%, GLU of 8.53%, PRO of 0.5%, GLY of 9.69%, ALA of 7.46%, VAL of 1.0%, MET of 4.38%, ISOLEU of 2.54%, LEU of 3.03%, TYR of 0.5%, PHE of 1.0%, HIS of 2.83%, LYS of 3.56%, TRP of 1.3% and ARG of 35.2%.

2. A polymeric anhydride of magnesium and proteic ammonium phospholinoleate with antiviral, antineoplastic and immunostimulant properties, as claimed in claim 1 which is produced by the process comprising the following steps:

biosynthesizing the polymeric anhydride from a selected line of Aspergillus sp in a culture medium of oat schaff and bouillon in a ratio of 100/1 of schaff to bouillon by fermenting the resulting mixture for a 120 hours at a temperature of 30°–35° C., a pH of the culture medium of 3–4, and having an aeration of 10 l/m and agitation of 40 rph restricted for the first 48 hours of the fermentation process to obtain a fermented mass, wherein the culture medium remains resting to the end of the fermentation process;

precipitating the polymeric anhydride in a basic pH of 11 after a mechanical separation of mycelium and washing the fermented mass with water and acetone in a ratio of 40:1 of water to acetone to form crystals of the polymeric anhydride;

washing the crystals of polymeric anhydride with sulphuric ether for removal of the impurities and then drying said crystals.

* * * * *